United States Patent [19]

Akashi et al.

[11] Patent Number: 5,300,257
[45] Date of Patent: Apr. 5, 1994

[54] 4,4'-BIPHENYLENEDIPHOSPHONITE COMPOUND AND USE THEREOF

[75] Inventors: Hiroyuki Akashi; Takeshi Inoue; Tetsuji Ike, all of Fukuoka; Hidaka Yasuhiro; Shoichi Horie, both of Osaka, all of Japan

[73] Assignee: Yoshitomi Pharmaceutical Industries, Ltd., Osaka, Japan

[21] Appl. No.: 888,925

[22] Filed: May 27, 1992

[30] Foreign Application Priority Data

May 27, 1991 [JP] Japan .................. 3-152618
Sep. 27, 1991 [JP] Japan .................. 3-277309

[51] Int. Cl.$^5$ .................. C07F 9/02; C09K 15/32; C09K 15/08
[52] U.S. Cl. .................. 252/400.24; 252/404; 252/406; 558/70; 558/197; 524/126; 524/151
[58] Field of Search .................. 524/126, 151, 135, 291; 558/70, 197; 252/400.24, 404, 406

[56] References Cited

U.S. PATENT DOCUMENTS 4,075,163 2/1978 Hofer et al. .................. 524/126
4,077,940 3/1978 Wedel .................. 260/45.7

FOREIGN PATENT DOCUMENTS 0251711 1/1988 European Pat. Off. .
2152481 4/1972 Fed. Rep. of Germany .
1372528 10/1974 United Kingdom .
2215727 9/1989 United Kingdom .
2227490 8/1990 United Kingdom .

Primary Examiner—Paul R. Michl
Assistant Examiner—Tae H. Yoon
Attorney, Agent, or Firm—Wenderoth, Lind & Ponack

[57] ABSTRACT

Tetrakis(2,4-di-tert-butyl-5-methylphenyl)-4,4'-biphenylenediphosphonite, stabilizers for organic materials, which contain said compound, and stabilized organic materials containing said compound as a stabilizer. The tetrakis(2,4-di-tert-butyl-5-methylphenyl)-4,4'-biphenylenediphosphonite has particularly superior hydrolysis resistance, and is characterized in that it has superior storage stability due to its scarce hygroscopicity. It can be purified and handled easily since it is in a powder form, and it shows less volatility at high temperatures. By using the compound of the present invention as a stabilizer for organic materials, extremely useful organic materials imparted with superior processing stability, heat resistance and resistance to oxidative degradation can be provided.

5 Claims, No Drawings

4,4'-BIPHENYLENEDIPHOSPHONITE COMPOUND AND USE THEREOF

FIELD OF THE INVENTION

The present invention relates to a novel 4,4'-biphenylenediphosphonite compound which is useful as a stabilizer for organic materials, and use thereof.

BACKGROUND OF THE INVENTION

Organic materials comprising natural polymers, synthetic polymers, fats and oils, lubricant oils and hydraulic oils, etc. are subject to oxidation resulting in lowered utility. Thus, various antioxidants have been devised and added to these organic materials. For example, it has been known that addition of stabilizers such as hindered phenolic compounds, thioalkanoic acid ester compounds, organic phosphorus compounds and aromatic amines solely or in combination can achieve a stabilizing effect.

In particular, synthetic resins such as polyethylene, polypropylene, acrylonitrile-butadiene-styrene resin and poly(vinyl chloride) resin are known to be degraded by the actions of heat, oxygen, light, etc., and result in extremely shortened life time due to color change and lowered mechanical strength. In order to prevent such degradation, there have been developed various kinds of antioxidants. Of those, phosphorus antioxidants have been widely used because of their superiority in preventing color change, and improved heat resistance and weathering resistance of resin given by them. Motivated by the increased demand in recent years for antioxidants having such superior heat resistance as to prevent volatilization at high temperatures, and superior processing stability, which has derived from the use of high temperatures for high speed molding and high temperature molding using alloys with engineering plastics, etc., phosphite and phosphonite compounds have been developed as phosphorous antioxidants and are on the market.

British Patent No. 1372528 discloses 4,4'-biphenylenediphosphonite compounds represented by tetrakis(2,4-di-tert-butylphenyl)-4,4'-biphenylenediphosphonite as a phosphorus antioxidant.

Also, GB A-2215727 discloses a composition containing tetrakis(2,4-di-tert-butylphenyl)-4,4'-biphenylenediphosphonite as a phosphorus antioxidant, and GB A-2227490 discloses a composition containing tetrakis(2,4-di-tert-butyl-6-methylphenyl)-4,4'-biphenylenediphosphonite as a phosphorus antioxidant.

Nonetheless, the widely-employed tetrakis(2,4-di-tert-butylphenyl)-4,4'-biphenylenediphosphonite is not sufficient in terms of hydrolysis resistance and heat stability of the compound itself and resistance to coloration and heat stability of the resin composition containing an active ingredient. In addition, the stabilizing effect by the aforementioned composition is not satisfactory.

SUMMARY OF THE INVENTION

In view of the present situation, the present inventors have conducted intensive studies and found that addition of a particular 4,4'-biphenylenediphosphonite compound which is superior in hydrolysis resistance and heat stability to an organic material could result in a well-balanced organic material improved in processing stability, heat resistance, and coloring degree at the initial stage and after heating. That is, the present invention relates to tetrakis(2,4-di-tert-butyl-5-methylphenyl)-4,4'-biphenylenediphosphonite, to a stabilizer for organic materials which comprises said compound, and to stabilized organic materials containing said compound as a stabilizer.

DETAILED DESCRIPTION OF THE INVENTION

Tetrakis(2,4-di-tert-butyl-5-methylphenyl)-4,4'-biphenylenediphosphonite of the present invention (hereinafter also referred to as the compound of the present invention) can be produced, for example, by the following methods.

Method 1: Biphenyl and halogenated phosphorus (e.g. phosphorus trichloride, phosphorus tribromide, phosphorus triiodide) are reacted in a gaseous phase at a high temperature or in the presence of a catalyst such as a Lewis acid (e.g. aluminium chloride, aluminium bromide, aluminium iodide, gallium chloride, gallium bromide, indium chloride, indium bromide, tin chloride, titanium chloride, zirconium chloride, rhodium chloride, antimony fluoride, antimony chloride, tungsten chloride, iron chloride, zinc chloride, boron fluoride, boron chloride, niobium chloride), preferably in a solvent (e.g. benzene, toluene, hexane, heptane, diethyl ether, tetrahydrofuran, chloroform, carbon tetrachloride, dichloroethane, chlorotoluene, chlorobenzene) under cooling or at a temperature in the range of from room temperature to the boiling point of the solvent used, preferably under reflux under heating, and 4,4'-biphenyldihalophosphine obtained and a stoichiometrical amount or more of 2,4-di-tert-butyl-5-methylphenol are reacted in the presence of an amine such as dimethylformamide, triethylamine, tributylamine, morpholine, dimethylaniline, pyridine, quinoline, collidine, aminopyridine, 1,8-bis(dimethylamino)naphthalene and 1,8-diazabicyclo[5.4.0]undec-7-en in a solvent such as benzene, toluene, hexane, heptane, diethyl ether, tetrahydrofuran, chloroform, carbon tetrachloride, dichloroethane, chlorotoluene and chlorobenzene under cooling or at a temperature in the range of from room temperature to the boiling point of the solvent used for 30 minutes to 24 hours to give the compound of the present invention.

Method 2: 4,4'-Dihalobiphenyl is reacted with magnesium under Grignard conditions to give a corresponding Grignard compound, which is then reacted with bis(2,4-di-tert-butyl-5-methylphenyl)chlorophosphide to give the compound of the present invention. This reaction is carried out, for example, in a non-polar organic solvent such as diethyl ether, dipropyl ether, ethylene glycol dimethyl ether, diethylene glycol dimethyl ether, dioxane and tetrahydrofuran at a temperature in the range of from room temperature to 120° C., preferably 30°–70° C. for 30 minutes to 24 hours.

The objective compound thus obtained can be purified by ordinary means such as recrystallization and chromatography.

The novel tetrakis(2,4-di-tert-butyl-5-methylphenyl)4,4'-biphenylenediphosphonite of the present invention is particularly superior in hydrolysis resistance, and is characterized in that it can be easily purified and easily handled since it is in the form of powder, is superior in storage stability due to little hygroscopicity, and shows less volatility at high temperatures. It is, therefore useful as a stabilizer for preventing oxidative degradation of organic materials.

In the present invention, reaction compositions containing tetrakis(2,4-di-tert-butyl-5-methyl-4,4'-phenyl)-biphenylenediphosphonite, bis(2,4-di-tert-butyl-5-methylphenyl)biphenylenephosphonite, tris(2,4-di-tert-butyl-5-methylphenyl)phosphite, and so on can be also used as stabilizers for preventing oxidative degradation or organic materials.

The organic materials to be stabilized by the compound of the present invention are exemplified by macromolecular polymers, fats and oils, mineral oils themselves and those comprising them, and examples of the macromolecular polymers include polyolefines such as α-olefin polymers (e.g. polyethylene, polypropylene, polybutene, polypentene and poly-3-methylbutylene), mixtures of polystyrene with polyethylene, polypropylene and/or other compatible polymers, and ethylene-vinyl acetate copolymers and ethylene-propylene copolymers, halogen-containing synthetic resins such as poly(vinyl chloride), poly(vinyl bromide), poly(vinyl fluoride), poly(vinylidene chloride), poly(vinylidene fluoride), chlorinated polyethylene, chlorinated polypropylene, brominated polyethylene, chlorinated rubber, vinyl chloride-vinyl acetate copolymers, vinyl chloride-ethylene copolymers, vinyl chloride-propylene copolymers, vinyl chloride-styrene copolymers, vinyl chloride-isobutylene copolymers, vinyl chloride-vinylidene chloride copolymers, vinyl chloride-styrene-maleic anhydride terpolymers, vinyl chloride-styrene-acrylonitrile terpolymers, vinyl chloride-butadiene copolymers, vinyl chloride-isobutylene copolymers, vinyl chloride-chlorinated propylene copolymers, vinyl chloride-vinylidene chloride-vinyl acetate terpolymers, vinyl chloride-acrylate copolymers, vinyl chloride-maleate copolymers, vinyl chloride-methacrylate copolymers, vinyl chloride-acrylonitrile copolymers and internally plasticized poly(vinyl chloride), petroleum resins, coumarone resins, polystyrene, copolymers of styrene and other monomer (e.g. maleic anhydride, butadiene, acrylonitrile), styrene resins such as acrylonitrile-butadiene-styrene resins, acrylate-butadiene-styrene resins and methacrylate-butadiene-styrene resins, poly(vinyl acetate), poly(vinyl alcohol), poly(vinyl formal), poly(vinyl butyral), acrylic resins, methacrylate resins, polyacrylonitrile, straight-chain polyesters, polyphenylene oxide, polyamides, polycarbonate, modified polyphenylene oxide, polyacetal, polyurethanes, cellulose resins, unsaturated polyester resins, phenol resins, urea resins, melamine resins, epoxy resins, silicone resins, polyethylene terephthalate, reinforced polyethylene terephthalate, polybutylene terephthalate, polysulfone resins, polyethersulfone, polyphenylene sulfide, polyetherketone, polyetherimide, polyoxybenzoyl, polyimide, polymaleimide and polyamideimide. Further, they may be natural rubber, synthetic rubbers such as isoprene rubber, butadiene rubber and acrylonitrile-butadiene copolymer rubber, or a blend of these resins. The aforementioned polyolefines may be those purified, after polymerization, to a small degree by removing residual catalyst, or those relatively highly purified, or polyolefines containing residual catalyst, which have undergone no removal process or only a simplified removal process for a highly active catalyst used. In particular, there can be used crystalline polyolefines obtained by using a Ziegler type catalyst where a halogen-containing magnesium compound is used as a catalyst carrier, and from which residual catalyst has not been removed yet (cf. U.S. Pat. No. 4,261,880).

More preferably, there are exemplified polyolefines such as polyethylenes (e.g. high density polyethylene, low density polyethylene, linear low density polyethylene, linear medium density polyethylene, etc.) and polypropylene, poly(vinyl chloride), acrylonitrile-butadiene-styrene resin, polycarbonate and modified polyphenylene oxide.

Where the compound of the present invention is used as a stabilizer for organic materials, it is preferably added in a proportion of 0.01–10% by weight relative to the organic materials, more preferably in a proportion of 0.01–5% by weight relative to the organic materials.

The stabilizer compound of the present invention in combination with phenolic antioxidants and/or sulfuric antioxidants gives superior heat stability to organic materials. When the compound of the present invention is combined with one or more of the phenolic antioxidants and/or sulfuric antioxidants and used as a stabilizer for organic materials, said antioxidants are preferably each added in a proportion of 0.01–10% by weight relative to the organic materials, more preferably in a proportion of 0.01–5% by weight relative to the organic materials.

When using the combination of the stabilizer of the present invention with phenolic antioxidants and/or sulfuric antioxidants, these components can be added separately or in the form of a mixture to the organic materials to be stabilized. The phenolic antioxidants and/or sulfuric antioxidants can be combined in a proportion of 0.1 to 10 times relative to the stabilizer of the present invention.

The phenolic antioxidants include 2,6-di-tert-butyl-4-methylphenol, 4-hydroxymethyl-2,6-di-tert-butylphenol, 2,6-di-tert-butyl-4-ethylphenol, butylated hydroxyanisole, n-oxtadecyl 3-(4-hydroxy-3,5-di-tert-butylphenyl)propionate, distearyl (4-hydroxy-3-methyl-5-tert-butyl)benzylmalonate, propyl gallate, octyl gallate, dodecyl gallate, tocopherol, 2,2'-methylenebis(4-methyl-6-tert-butylphenol), 2,2'-methylenebis(4-ethyl-6-tert-butylphenol), 4,4'-methylenebis(2,6-di-tert-butylphenol), 4,4'-butylidenebis(6-tert-butyl-m-cresol), 4,4'-thiobis(6-tert-butyl-m-cresol), stylenated phenol, N,N-hexamethylenebis(3,5-di-tert-butyl-4-hydroxyhydrocinnamide), calcium bis(3,5-di-tert-butyl-4-hydroxybenzylphosphonic acid ethyl ester), 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tetrakis[3-(3,5-di-tert-butyl-4-hydroxyphenyl)propionyloxymethyl]methane, 1,6-hexanediol-bis[3-(3,5-di-tert-butyl-4-hydroxyphenyl)propionate], 2,2'-methylenebis(4-methyl-6-cyclohexylphenol), 2,2'-methylenebis[6-(1-methylcyclohexyl)-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)isocyanuric acid, triethylene glycol-bis[3-(3-tert-butyl-4-hydroxy-5-methylphenyl)]propionate, 2,2'-oxamidebis[ethyl 3-(3,5-di-tert-butyl-4-hydroxyphenyl)propionate], 6-(4-hydroxy-3,5-di-tert-butylanilino)-2,4-dioctylthio-1,3,5-triazine, bis[2-tert-butyl-4-methyl-6-(2-hydroxy-3-tert-butyl-5-methylbenzyl)phenyl]terephthalate, 3,9-bis[2-[3-(3-tert-butyl-4-hydroxy-5-methylphenyl)propionyloxy]-1,1-dimethylethyl]-2,4,8,10-tetraoxaspiro[5.5]undecane or 3,9-bis[2-[3-(3,5-di-tert-butyl-4-hydroxyphenol)propionyloxy]-1,1-dimethylethyl]-2,4,8,10-tetraoxaspiro[5.5]undecane, to which they are not limited.

The preferable phenolic antioxidants include 2,6-di-tert-butyl-4-methylphenol, octadecyl 3-(4-hydroxy-3,5- di-tert-butylphenyl)propionate, tetrakis[3-(3,5-di-tert-butyl-4-hydroxyphenyl)propionyloxymethyl]methane, triethylene glycolbis[3-(3,5-di-tert-butyl-4-hydroxy-5-methylphenyl)propionate, 4,4'-butylidenebis(6-tert-butyl-m-cresol), 4,4'-thiobis(6-tert-butyl-m-cresol), 1,3,5-tris(3,5-di-tert-butyl-4-hydroxybenzyl)isocyanuric acid, 1,1,3-tris(2-methyl-4-hydroxy-5-tertbutylphenyl)-butane or 3,9-bis[2-[3-(3-tert-butyl-4-hydroxy-5-methylphenyl)propionyloxy]-1,1-dimethylethyl]-2,4,8,10-tetraoxaspiro[5.5]undecane.

The sulfuric antioxidant is an ester of thioalkanoic acid, such as dilauryl ester, dimyristyl ester, distearyl ester and didocosyl ester, and an ester with polyhydric alcohol such as glycerol, trimethylolethane, trimethylolpropane, pentaerythritol and trishydroxyethylisocyanurate.

Preferred are dilauryl thiodipropionate, dimyristyl thiodipropionate, distearyl thiodipropionate and pentaerythritol-tetrakis($\beta$-lauryl thiopropionate).

Also, ultraviolet absorbers and light stabilizers can be used in combination with the stabilizer compound of the present invention for improving weather resistance of the organic materials.

Examples of such ultraviolet absorber and light stabilizer include salicylic acid compounds, benzophenone compounds, benzotriazole compounds, cyanoacrylate compounds, nickel compounds and 2,2,6,6-tetramethylpiperizine compounds such as phenyl salicylate, p-tert-butylphenyl salicylate, p-octylphenyl salicylate, 2,4-dihydroxybenzophenone, 2-hydroxy-4-acetoxyethoxybenzophenone, 2-hydroxy-4-methoxybenzophenone, 2,2'-dihydroxy-4,4'-dimethoxybenzophenone, 2-hydroxy-4-n-octyloxybenzophenone, 2-hydroxy-4-isooctyloxybenzophenone, 2-hydroxy-4-dodecyloxybenzophenone, 2-hydroxy-4-oxtadecyloxybenzophenone, disodium 2,2'-dihydroxy-4,4'-dimethoxy-5,5'-disulfobenzophenone, 2-hydroxy-4-(2-hydroxy-3-methacryloxy)propoxybenzophenone, 2-(2-hydroxy-5-methylphenyl)benzotriazole, 2-(2-hydroxy-3,5-di-tert-butylphenyl)benzotriazole, 2-(2-hydroxy-3-tert-butyl-5-methylphenyl)-5-chlorobenzotriazole, 2-(2-hydroxy-3,5-di-tert-butylphenyl)-5-chlorobenzotriazole, 2-(2-hydroxy-3,5-di-tert-butylphenyl)-5-chlorobenzotriazole, 2-(2-hydroxy-5-tert-octylphenyl)benzotriazole, n-hexadecyl 3,5-di-tert-butyl-4-hydroxybenzoate, 2,4-di-tertbutylphenyl 3,5-di-tert-butyl-4-hydroxybenzoate, ethyl 2-cyano-3,3-diphenylacrylate, nickel [2,2'-thiobis{4-(1,1,3,3-tetramethylbutyl)phenolate}]-n-butylamine, nickel [2,2'-thiobis{4-(1,1,3,3-tetramethylbutyl)phenolate}], nickel-bis(3,5-di-tert-butyl-4-hydroxybenzylphosphonic acid ethyl ester, bis(2,2,6,6-tetramethyl-4-piperidyl)sebacate, bis(1,2,2,6,6-pentamethyl-4-piperidyl)-2-(3,5-di-tert-butyl-4-hydroxybenzyl)-2-n-butylmalonate, bis(1-acryloyl-2,2,6,6-tetramethyl-4-pyperidyl) bis(3,5-di-tert-butyl-4-hydroxybenzyl)malonate, tetrakis(2,2,6,6-tetramethyl-4-piperidyl)-1,2,3,4-butanetetracarboxylate, poly{[6-(1,1,3,3-tetramethylbutyl)imino-s-triazine-2,4-diyl][(2,2,6,6-tetramethyl-4-piperidyl)imino]hexamethylene(2,2,6,6-tetramethyl-4-piperidyl)imino}, poly{(6-morpholino-s-triazine-2,4-diyl)[(2,2,6,6-tetramethyl-4-piperidyl)imino]hexamethylene[(2,2,6,6-tetramethyl-4-piperidyl)imino]}, 1-hydroxyethyl-2,2,6,6-tetramethyl-4-piperidinol, succinic acid condensate and cyanuric chloride/tertiary octylamine 1,6-bis(2,2,6,6-tetramethyl-4-piperidylamino)hexane condensate.

Preferred are 2-hydroxy-4-n-octyloxybenzophenone, 2-(2-hydroxy-5-methylphenyl)benzotriazole, 2-(2-hydroxy-3-tertbutyl-5-methylphenyl)-5-chlorobenzotriazole, 2-(2-hydroxy-3,5-di-tert-butylphenyl)-5-chlorobenzotriazole, bis(2,2,6,6-tetramethyl-4-piperidyl)sebacate, poly{[6-(1,1,3,3-tetramethylbutyl)imino-s-triazine-2,4-diyl][(2,2,6,6-tetramethyl-4-piperidyl)imino]hexamethylene(2,2,6,6-tetramethyl-4-piperizyl)imino}.

The compound of the present invention may be used in combination with other phosphorus antioxidants, and such phosphorus antioxidants include tris-(2,4-di-tert-butylphenyl)phosphite, tris-(2,4-di-tert-butyl-5-methylphenyl)phosphite, tetrakis(2,4-di-tert-butylphenyl)-4,4'-biphenylenediphosphonite, bis-(2,4-di-tert-butylphenyl)pentaerythritoldiphosphite, bis-(2,6-di-tert-butyl-4-methylphenyl)pentaerythritoldiphosphite and 2,2'-methylenebis(4,6-di-tert-butylphenyl)-2-ethylhexylphosphite.

When the compound of the present invention is used in combination with one or more of the ultraviolet absorbers, light stabilizers and phosphorus antioxidants, and used as a stabilizer for organic materials, said stabilizers are each preferably added in a proportion of 0.01–10% by weight relative to the organic materials, more preferably in a proportion of 0.01–5% by weight relative to the organic materials.

Thus, the present invention also provides a stabilizer for organic materials, which comprises tetrakis(2,4-di-tert-butyl-5-methylphenyl)-4,4'-biphenylenediphosphonite, and at least one member selected from the group consisting of a phenolic antioxidant, a sulfuric antioxidant, an ultraviolet absorber, a light stabilizer and a phosphorus antioxidant.

The method for adding the compound of the present invention solely or in combination with other antioxidants and/or stabilizers such as ultraviolet absorbers and light stabilizers includes mixing, then kneading and extrusion.

The compound of the present invention can be used with metallic soap, heavy metal inactivating agent, nucleating agent, organotin stabilizer, plasticizer, epoxide, pigment, filler, blowing agent, anti-static agent, flame retardant, lubricant and processing aid.

The present invention is hereinbelow described in detail by illustrating example and experiment examples, to which the invention is not limited.

EXAMPLE 1

(1) Biphenyl (4.6 g) and phosphorus trichloride (65.9 g) were dissolved, and aluminum chloride (10.7 g) was added thereto, followed by refluxing for 5 hours. After cooling, the mixture was further cooled to 5° C. or below, and phosphorus oxychloride (12.3 g) was dropwise added thereto, followed by 0.5 hour of reaction. The aluminum chloride-phosphorus oxychloride complex obtained was filtrated, washed thoroughly with chlorobenzene, and the filtrate was concentrated under reduced pressure to give red-yellow, viscous 4,4'-biphenylenebis(dichlorophosphine).

(2) 2,4-Di-tert-butyl-5-methylphenol (17.6 g) and triethylamine (8.1 g) were dissolved in toluene (80 g), and the mixture was cooled to 5° C. or below. The 4,4'-biphenylenebis(dichlorophosphine) (7.6 g) obtained in (1) in toluene (50 g) was dropwise added thereto, followed by reaction at 40°–60° C. for 6 hours. After the reaction, it was left cooling, and triethylamine hydrochloride was filtrated. The filtrate was concentrated under reduced pressure, recrystallized from acetonitrile/toluene, and dried to give 7 g of tetrakis(2,4-ditert-butyl-5-methylphenyl)-4,4'-biphenylenediphosphonite as white crystals, m.p. 212°–214° C. The compound obtained was confirmed to be the objective tetrakis(2,4-di-tert-butyl-5-methylphenyl)-4,4'-biphenylenediphosphonite by infrared absorption spectrum, nuclear magnetic resonance spectrum, mass spectrum, elemental analysis, and so on.

The effect of the present invention is described in the following Experiment Examples.

EXPERIMENT EXAMPLE 1

1. Hydrolysis: A phosphorus antioxidant was left standing in a thermostatic chamber of 75% relative humidity at 40° C. in an open state, and periodically sampled. The phenol produced by decomposition was measured by high performance liquid chromatography (HPLC), and percent decomposition was determined.

2. Heat volatility: Weight-decrease starting temperature (° C.) and the temperature at which the weight reduced to 50% (° C.) were determined by thermogravimetric analysis under a nitrogen atmosphere at a temperature elevating speed of 10° C./min.

In the following Table, Comparative Examples 1–3 are the following compounds. (The same in the following Experiment Examples.)

Compound of Comparative Example 1: tetrakis(2,4-di-tert-butylphenyl)-4,4'-biphenylenediphosphonite
Compound of Comparative Example 2: bis(2,4-di-tert-butylphenyl)pentaerythritoldiphosphite
Compound of Comparative Example 3: tris(2,4-di-tert-butylphenyl)phosphite The results are shown in Table 1.

TABLE 1

| | Hydrolysis (%) | | | Heat volatility (°C.) | |
|---|---|---|---|---|---|
| | 1 week later | 2 week later | 3 week later | Initiation of weight reduction | 50% reduction |
| Compound of Invention | 0.7 | 0.7 | 0.8 | 293 | 412 |
| Comparative Ex. 1 | 0.8 | 2.6 | 10.1 | 218 | 392 |
| Comparative Ex. 2 | 22 | not tested | not tested | 82 | 273 |
| Comparative Ex. 3 | 0.8 | 6.3 | 8.5 | 184 | 308 |

As shown in Table 1, the compound of the present invention was scarcely hydrolyzed even after 3 weeks, thereby exhibiting superior action and effect in hydrolysis resistance, in which property the known phosphorus antioxidants of Comparative Examples are poor. It is evident that the compound of the present invention is a phosphorus antioxidant with superior stability. In particular, the compound of the present invention retained superior stability in volatility at high temperatures as compared with the analogous compound of Comparative Example 1.

EXPERIMENT EXAMPLE 2

The compounds as shown in the following Formulation Example were respectively added to polypropylene (homopolymer) added with no additive, and the mixture was mixed in a mixer for 5 minutes, after which pellets were extruded by an extruder (20 mm φ) at a die temperature of 280° C. Using these pellets, heat stability (determinations of heat degradation initiation time when keeping at 220° C. under an air atmosphere, weight-decrease starting time by a heat analyzer, and oxygen absorption induction period at 190° C. by macromolecule degradation measurement apparatus) was determined. Also, from these pellets, a test piece was produced by an injection molding machine (59×90×1 mm at 200° C., 35 kg/cm$^2$), which was then used for the measurement of brittle point (BP, time) in a Geer oven.

FORMULATION EXAMPLE

| | |
|---|---|
| Polypropylene (homopolymer) | 99.7% by weight |
| Test Compound | 0.1% by weight |
| Tetrakis[3-(3,5-di-tert-butyl-4-hydroxyphenyl)propionyloxymethyl]methane | 0.1% by weight |
| Calcium stearate | 0.1% by weight |

The results are shown in Table 2.

TABLE 2

| | Pellet | | | Test piece |
|---|---|---|---|---|
| | Heat stability | | Oxygen absorption Induction Period (min) | Heat stability BP (hr) |
| | Initiation of Degradation (min) | Initiation of weight reduction (min) | | |
| Compound of Invention | 55.4 | 58.5 | 92 | 1650 |
| Comparative Ex. 1 | 47.7 | 51.2 | 67 | 1500 |

As shown in Table 2, the compound of the present invention is superior to the compound of Comparative Example 1 in stability as determined by the heat analysis of the pellets, and brittle time of the pellets at 150° C. In addition, oxygen induction period was longer than that of the compound of Comparative Example 1. This indicates that the compound of the present invention is superior in heat stability and antioxidative action.

EXPERIMENT EXAMPLE 3

The compounds as shown in the following Formulation Example were respectively added to a low density polyethylene resin added with no additive, and the mixture was mixed in a mixer for 5 minutes, after which pellets were produced by an extruder (20 mm φ) at a die temperature of 230° C. Using these pellets, heat stability (determination of oxygen absorption induction period at 190° C. by the macromolecule degradation measurement apparatus) and coloration by kneading (determination of yellowness index, YI, by colorimeter) were determined.

FORMULATION EXAMPLE

| | |
|---|---|
| Low density polyethylene resin | 99.8% by weight |
| Test Compound | 0.05% by weight |
| Tetrakis[3-(3,5-di-tert-butyl-4-hydroxyphenyl)propionyloxymethyl]methane | 0.05% by weight |
| Calcium stearate | 0.1% by weight |

The results are shown in Table 3.

TABLE 3

| | Pellet | |
|---|---|---|
| | Oxygen absorption Induction Period (min) | Coloration by kneading YI |
| Compound of Invention | 145 | 2.6 |
| Comparative | 123 | 4.6 |

TABLE 3-continued

|  | Pellet | |
| --- | --- | --- |
|  | Oxygen absorption Induction Period (min) | Coloration by kneading YI |
| Ex. 1 | | |

As shown in Table 3, the compound of the present invention showed less coloring and longer oxygen induction period than the compound of Comparative Example 1, and is superior in heat stability and antioxidative action.

EXPERIMENT EXAMPLE 4

The compounds as shown in the following Formulation Example were respectively added to poly(vinyl chloride) resin (manufactured by Kyodo Vinyl, Japan), and the mixture was kneaded by an open roll mill for 3 minutes, after which it was press molded by a pressing machine at 170° C. for 5 minutes to give a 1 mm-thick test piece. Thereafter, the test piece was subjected to a heat degradation test in a Geer oven at 170° C., and the time to blacken all over the surface of the test piece (degradation time) was measured.

FORMULATION EXAMPLE

| Poly(vinyl chloride) | 100 parts by weight |
| --- | --- |
| Test Compound | 0.5 part by weight |
| Dioctyl phthalate | 50 parts by weight |
| Epoxidized soybean oil | 2 parts by weight |
| Barium stearate | 0.35 part by weight |
| Calcium stearate | 0.25 part by weight |

The results are shown in Table 4.

TABLE 4

|  | Degradation time (min) |
| --- | --- |
| Compound of Invention | 100 |
| Comparative Ex. 1 | 80 |

As shown in Table 4, the compound of the present invention has superior heat stability as compared with the compound of Comparative Example 1.

EXPERIMENT EXAMPLE 5

The compounds as shown in the following Formulation Example were respectively added to a high density polyethylene resin added with no additive, and the mixture was mixed in a mixer for 5 minutes, after which it was extruded into pellets by a 20 mm $\phi$ extruder (resin temperature: 230° C., residence time: constant, repetition: 5 times). Using these pellets, melt viscosity was determined by a flow tester (190° C., LOAD 2,000 kgf, DIA 2.095 mm).

FORMULATION EXAMPLE

| High density polyethylene resin | 99.7% by weight |
| --- | --- |
| Test Compound | 0.1% by weight |
| n-Octadecyl 3-(4-hydroxy-3,5-di-tert-butylphenyl)propionate | 0.1% by weight |
| Calcium stearate | 0.1% by weight |

In the Table, Comparative Example 4 is the following compound.

Compound of Comparative Example 4: bis(2,6-di-tert-butyl-4-methylphenyl)pentaerythritol diphosphite.

The results are shown in Table 5.

TABLE 5

|  | Viscosity VI (poise) | |
| --- | --- | --- |
|  | n = 1 | n = 5 |
| Compound of Invention | 88020 | 91440 |
| Comparative Ex. 1 | 88840 | 93110 |
| Comparative Ex. 2 | 95020 | 97190 |
| Comparative Ex. 3 | 90760 | 93440 |

As shown in Table 5, the compound of the present invention gave a melt viscosity lower than that of the compound of Comparative Example to the pellets extruded 5 times, and is superior in processing stability.

EXPERIMENT EXAMPLE 6

The compounds as shown in the following Formulation Example were respectively added to a mixed resin (1/1) of polyphenylene oxide (PPO)/polystyrene (PS), and the mixture was mixed in a mixer for 5 minutes. Using Brabender Plastograph, color change upon kneading for a certain time at 280° C.×50 rpm was visually observed.

FORMULATION EXAMPLE

| PPO/PS mixed resin (1/1) | 100 parts by weight |
| --- | --- |
| Test Compound | 0.05 part by weight |

The results are shown in Table 6.

TABLE 6

|  | Color change | | |
| --- | --- | --- | --- |
|  | 5 min. later | 10 min. later | 30 min. later |
| Compound of Invention | pale oscher | pale oscher | brown |
| Comparative Ex. 1 | oscher | yellowish brown | blackish brown |
| Comparative Ex. 3 | pale oscher | oscher | blackish brown |
| Comparative Ex. 4 | oscher | yellowish brown | blackish brown |

As shown in Table 6, the compound of the present invention showed less coloring than the compound of Comparative Example, and is superior in processing stability.

EXPERIMENT EXAMPLE 7

The compounds as shown in Table 7 were respectively added to polycarbonate resin powder (manufactured by Mitsubishi Gasu Kagaku, Japan), and the mixture was mixed in a tumbler mixer for 5 minutes, after which it was extruded into pellets by a 20 mm $\phi$ extruder (resin temperature: 290° C.). Using these pellets, a 3 mm-thick test piece was produced by a screw injection molding machine (resin temperature: 280° C.), and yellowness index (YI) was measured by a colorimeter. Also, YI in a Geer oven at 150° C.×76 hr was measured.

FORMULATION EXAMPLE

| Polycarbonate resin | 99.85% by weight |
| --- | --- |
| Test Compound | 0.05% by weight |
| 1,3,5-tris(3,5-di-tert-butyl-4-hydroxybenzyl)isocyanuric acid | 0.05% by weight |
| Dilauryl thiodipropionate | 0.05% by weight |

The results are shown in Table 7.

TABLE 7

|  | Injection Molded Product (test piece) (YI) | Upon 76 hrs' heat treatment of test piece at 150° C. (YI) |
|---|---|---|
| Compound of Invention | 6.0 | 7.0 |
| Comparative Ex. 1 | 7.8 | 12.0 |
| Comparative Ex. 2 | 6.8 | 8.4 |
| Comparative Ex. 3 | 7.3 | 8.5 |
| Comparative Ex. 4 | 6.4 | 8.4 |

As shown in Table 7, the compound of the present invention showed less coloring than the compounds of Comparative Examples, and gives superior heat stability to the polycarbonate resin.

EXPERIMENT EXAMPLE 8

The compounds as shown in Table 8 were respectively added to acrylonitrile-butadiene-styrene resin powder, and mixed in a tumbler mixer for 5 minutes, after which it was extruded into pellets by a 20 mm $\phi$ extruder (resin temperature: 220° C.). Using these pellets, a 3 mm-thick test piece was produced by a screw injection molding machine (resin temperature: 250° C.), which was then heat-treated in a Geer oven at 100° C. for 100 hours. The yellowness index (YI) before and after the heat treatment was measured.

FORMULATION EXAMPLE

| Acrylonitrile-butadiene-styrene resin | 99.7% by weight |
|---|---|
| Test Compound | 0.1% by weight |
| 1,1,3-Tris(2-methyl-4-hydroxy-5-tert-butylphenyl)butane | 0.1% by weight |
| Distearyl thiodipropionate | 0.1% by weight |

The color change ($\Delta$YI) results are shown in Table 8.

TABLE 8

|  | Color Change ($\Delta$YI) |
|---|---|
| Compound of Invention | 9 |
| Comparative Ex. 1 | 13 |
| Comparative Ex. 5 | 15 |

In the Table, the compound of Comparative Example 5 is the following compound.
Compound of Comparative Example 5: 2,2'-methylenebis(4,6-di-tert-butylphenyl)-2-ethylhexyl phosphite.

As shown in Table 8, the compound of the present invention showed less coloring than the compounds of Comparative Examples, and gives superior heat stability to the acrylonitrile-butadiene-styrene resin.

EXPERIMENT EXAMPLE 9

The compounds as shown in Table 9 were respectively added to polypropylene resin added with no additive, and the mixture was mixed in a tumbler mixer for 5 minutes, after which it was extruded into pellets by a 20 mm $\phi$ extruder (resin temperature: 280° C., residence time: constant, repetition: 4 times). Using these pellets, melt viscosity was determined by a flow tester (230° C., LOAD 2,000 kgf, DIA 2.095 mm).

FORMULATION EXAMPLE

| Polypropylene resin | 99.5% by weight |
|---|---|
| Test Compound | 0.1% by weight |
| 3,9-Bis[2-{3-(3-tert-butyl-4-hydroxy-5-methylphenyl)propionyloxy}-1,1-dimethyl-ethyl]-2,4,8,10-tetraoxaspiro[5.5]undecane | 0.1% by weight |
| Pentaerythritol-tetrakis($\beta$-laurylthio-propionate) | 0.2% by weight |
| Calcium stearate | 0.1% by weight |

The results are shown in Table 9.

TABLE 9

|  | Viscosity VI (poise) | |
|---|---|---|
|  | n = 1 | n = 4 |
| Compound of Invention | 26857 | 21220 |
| Comparative Ex. 1 | 26977 | 18877 |
| Comparative Ex. 5 | 25210 | 19330 |

As shown in Table 9, the compound of the present invention caused less lowering of the melt viscosity of the pellets extruded 4 times, as compared with the compounds of Comparative Examples, and gives superior processing stability to the polypropylene resin containing a phenolic antioxidant and a sulfuric antioxidant in combination.

EXPERIMENT EXAMPLE 10

The compounds as shown in Table 10 were respectively added to a polypropylene resin added with no additive, and the mixture was mixed in a tumbler mixer for 5 minutes, after which it was extruded into pellets by a 20 mm $\phi$ extruder (resin temperature: 280° C., residence time: constant, repetition: 4 times). Using these pellets, melt viscosity was determined by a flow tester (230° C., LOAD 2,000 kgf, DIA 2.095 mm). Also, yellowness index (YI) of the extruded pellets was measured.

FORMULATION EXAMPLE

| Polypropylene resin | 99.6% by weight |
|---|---|
| Test compound | 0.1% by weight |
| Tetrakis[3-(3,5-di-tert-butyl-4-hydroxyphenyl)propionyloxymethyl]methane | 0.1% by weight |
| Light stabilizers and/or ultraviolet absorbers | 0.1% by weight |
| Calcium stearate | 0.1% by weight |

The light stabilizers (HALS) or ultraviolet absorbers (UVA) in the Table are the following compounds.
HALS(1): bis(2,2,6,6-tetramethyl-4-piperidyl)sebacate
HALS(2): poly[{6-(1,1,3,3,-tetramethylbutyl)imino-s-triazin-2,4-diyl}{2,2,6,6-tetramethyl-4-piperidyl)imino}hexamethylene{2,2,6,6-tetramethyl-4-piperidyl)imino}]
UVA(1): 2-(2-hydroxy-3-tert-butyl-5-methylphenyl)-5-chlorobenzotriazole.

The results are shown in Table 10.

TABLE 10

|  | Viscosity VI (poise) | | Yellowness Index |
|---|---|---|---|
|  | n = 1 | n = 4 | YI |
| Compound of Invention + HALS (1) | 24103 | 13393 | 1.8 |
| Comparative | 24833 | 12867 | 3.1 |

TABLE 10-continued

| | Viscosity VI (poise) | | Yellowness Index |
|---|---|---|---|
| | n = 1 | n = 4 | YI |
| Ex. 1 + HALS (1) | | | |
| Comparative Ex. 5 + HALS (1) | 22630 | 12243 | 3.1 |
| Compound of Invention + HALS (2) | 22993 | 5000 | 2.1 |
| Comparative Ex. 1 + HALS (2) | 21990 | 3918 | 2.1 |
| Comparative Ex. 5 + HALS (2) | 20560 | 4435 | 3.4 |
| Compound of Invention + HALS (1) 0.75 UVA (1) 0.25 | 23843 | 11323 | 6.3 |
| Comparative Ex. 1 + HALS (1) 0.75 UVA (1) 0.25 | 22630 | 9050 | 7.8 |
| Comparative Ex. 5 + HALS (1) 0.75 UVA (1) 0.25 | 23543 | 11290 | 7.5 |

(In Table 10, n means repetition number of extrusion.)

As shown in Table 10, the compound of the present invention caused less lowering of the melt viscosity and less coloration by kneading as shown in small YI of the pellets extruded 4 times, as compared with the compounds of Comparative Examples, and gives superior processing stability to the polypropylene resin containing a phenolic antioxidant, light stabilizers and/or ultraviolet absorbers in combination.

EXPERIMENT EXAMPLE 11

The compounds as shown in Table 11 were respectively added to a linear low density polyethylene resin added with no additive, and the mixture was mixed in a mixer for 5 minutes, after which pellets were prepared therefrom by a 20 mm$\phi$ extruder (resin temperature: 250° C., residence time: constant). Using these pellets, torque change was measured by Brabender Plastograph, and the time to a sudden decrease of torque was taken as degradation time (200° C., rotation: 50 rpm).

FORMULATION EXAMPLE

| | |
|---|---|
| Linear low density polyethylene resin | 99.72% by weight |
| Test Compound | 0.08% by weight |
| Calcium stearate | 0.1% by weight |
| n-Octadecyl 3-(4-hydroxy-3,5-di-tert-butylphenol)propionate | 0.1% by weight |

As the linear low density polyethylene resin, used was a 20% mixture of low density polyethylene resin.
The results are shown in Table 11.

TABLE 11

| | Degradation time (min) |
|---|---|
| Compound of Invention | 11.2 |
| Comparative Ex. 1 | 10.2 |
| Comparative Ex. 2 | 6.7 |
| Comparative Ex. 3 | 7.8 |
| Comparative Ex. 4 | 9.5 |
| Comparative Ex. 5 | 9.7 |

As shown in Table 11, the compound of the present invention showed longer time to degradation as compared with the compounds of Comparative Examples, and gives superior heat stability to the linear low density polyethylene resin.

EXPERIMENT EXAMPLE 12

The compounds as shown in Table 12 were respectively added to a polypropylene resin added with no additive, and the mixture was mixed in a tumbler mixer for 5 minutes, after which it was extruded into pellets by a 20 mm$\phi$ extruder (resin temperature: 260° C., residence time: constant). Using these pellets, a 3 mm-thick test piece was produced by a screw injection molding machine (200° C., injection pressure: 30 kg/cm$^2$), which was then subjected to the determinations of yellowness index (YI) and brittle time at 150° C.

FORMULATION EXAMPLE

| | |
|---|---|
| Polypropylene resin | 73.65% by weight |
| Test Compound | 0.1% by weight |
| Tetrakis[3-(3,5-di-tert-butyl-4-hydroxyphenyl)propionyloxymethyl]methane | 0.1% by weight |
| Distearyl thiodipropionate | 0.3% by weight |
| N-(1H-1,2,4-triazol-3-yl)salicylamide (heavy metal inactivating agent) | 0.75% by weight |
| Talc | 25% by weight |
| Calcium stearate | 0.1% by weight |

The results are shown in Table 12.

TABLE 12

| | Yellowness Index (YI) | Brittle Time (hr) |
|---|---|---|
| Compound of Invention | 26.4 | 750 |
| Comparative Ex. 1 | 28.3 | 700 |
| Comparative Ex. 5 | 30.5 | 660 |

As shown in Table 12, the compound of the present invention gives less coloration and superior heat stability to the polypropylene resin in combination with a phenolic antioxidant, a sulfuric antioxidant, a heavy metal inactivating agent and talc (filler) as compared with the compounds of Comparative Examples.

Tetrakis(2,4-di-tert-butyl-5-methylphenyl)-4,4'-biphenylenediphosphonite of the present invention possesses various beneficial characteristics overcoming the defects of known phosphorus antioxidants. It has superior hydrolysis resistance and good storage stability, it can be purified and handled easily, since it is in a powder form, it is scarcely hygroscipic, and it shows less volatility at high temperatures. By using the compound of the present invention as a stabilizer for organic materials, extremely useful organic materials imparted with superior processing stability, heat resistance and stability to oxidative degradation can be provided.

What is claimed is:
1. Tetrakis(2,4-di-tert-butyl-5-methylphenyl)-4,4'-biphenylenediphosphonite.
2. A stabilizer composition for organic materials, which comprises an effective amount of tetrakis(2,4-di-tert-butyl-5-methylphenyl)-4,4'-biphenylenediphosphonite.
3. A stabilizer composition for organic materials, which comprises tetrakis(2,4-di-tert-butyl-5-methylphenyl)-4,4'-biphenylenediphosphonite, and at least one member selected from the group consisting of a phenolic antioxidant, a sulfuric antioxidant, an ultraviolet absorber, a light stabilizer and a phosphorus antioxidant.

4. A stabilizer composition for organic materials according to claim 3, wherein the phenolic antioxidant is 2,6-di-tert-butyl-4-methylphenol, 4-hydroxymethyl-2,6-di-tert-butylphenol, 2,6-di-tert-butyl-4-ethylphenol, butylated hydroxyanisole, n-oxtadecyl 3-(4-hydroxymethyl-5-tert-butyl)benzylmalonate, propyl gallate, octyl gallate, dodecyl gallate, tocopherol, 2,2'-methylenebis(4-methyl-6-tert-butylphenol), 2,2'-methylenebis(4-ethyl-6-tert-butylphenol), 4,4'-methylenebis(2,6-di-tert-butylphenol), 4,4'-butylidenebis(6-tert-butyl-m-cresol), 4,4'-thiobis(6-tert-butyl-m-cresol), stylenated phenol, N,N-hexamethylenebis(3,5-di-tert-butyl-4-hydroxyhydrocinnamide), calcium bis(3,5-di-tert-butyl-4-hydroxybenzylphosphonic acid ethyl ester, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tetrakis-[3-(3,5-di-tert-butyl-4-hydroxyphenyl)propionyloxymethyl]methane, 1,6-hexanediol-bis[3-(3,5-di-tert-butyl-4-hydroxyphenyl)propionate], 2,2'-methylenebis(4-methyl-6-cyclohexylphenol), 2,2'-methylenebis[6-(1-methylcyclohexyl)-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)isocyanuric acid, triethylene glycol-bis[3-(3-tert-butyl-4-hydroxy-5-methylphenyl)]propionate, 2,2'-oxamidebis[ethyl-3-(3,5-di-tert-butyl-4-hydroxyphenyl)propionate], 6-(4-hydroxy-3,5-di-tert-butylanilino)-2,4-dioctylthio-1,3,5-triazine, bis[2-tert-butyl-4-methyl-6-(2-hydroxy-3-tert-butyl-5-methylbenzyl)phenyl]terephthalate, 3,9-bis[2-[3-(3-tert-butyl-4-hydroxy-5-methylphenyl)propionyloxy]-1,1-dimethylethyl]-2,4,8,10-tetraoxaspiro[5.5]undecane or 3,9-bis[2-[3-(3,5-di-tert-butyl-4-hydroxyphenyl)propionyloxy]-1,1-dimethylethyl]-2,4,8,10-tetraoxaspiro[5.5]undecane.

5. A stabilizer composition for organic materials according to claim 3, wherein the phenolic antioxidant is 2,6-di-tert-butyl-4-methylphenol, octadecyl 3-(4-hydroxy-3,5-di-tert-butylphenyl)propionate, tetrakis[3-(3,5-di-tert-butyl-4-hydroxyphenyl)propionyloxymethyl]methane, triethylene glycolbis[3-(3,5-di-tert-butyl-4-hydroxy-5-methylphenyl)propionate, 4,4'-butylidenebis(6-tert-butyl-m-cresol), 4,4'-thiobis(6-tert-butyl-m-cresol), 1,3,5-tris(3,5-di-tert-butyl-4-hydroxybenzyl)isocyanuric acid, 1,1,3-tris(2-methyl-4-hydroxy-5-tert-butylphenyl)butane or 3,9-bis[2-[3-(3-tert-butyl-4-hydroxy-5-methylphenyl)propionyloxy]-1,1-dimethylethyl]-2,4,8,10-tetraoxaspiro[5.5]undecane.

* * * * *

UNITED STATES PATENT AND TRADEMARK OFFICE
CERTIFICATE OF CORRECTION

PATENT NO. : 5,300,257
DATED : April 5, 1994
INVENTOR(S) : HIROYUKI AKASHI, TAKESHI INOUE, TETSUJI IKE, YASUHIRO HIDAKA and SHOICHI HORIE It is certified that error appears in the above-indentified patent and that said Letters Patent is hereby corrected as shown below:

On the title page of the patent, correct the name of the fourth-listed inventor to read YASUHIRO HIDAKA.

Signed and Sealed this

Twenty-fifth Day of October, 1994

Attest:

BRUCE LEHMAN

*Attesting Officer*   *Commissioner of Patents and Trademarks*